US00PP20281P3

(12) United States Plant Patent
Sheehan

(10) Patent No.: US PP20,281 P3
(45) Date of Patent: Sep. 8, 2009

(54) GRAPEVINE 'SHEEGENE-8'

(50) Latin Name: *Vitis vinifera*
Varietal Denomination: Sheegene-8

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 50 days.

(21) Appl. No.: 11/897,631

(22) Filed: Aug. 30, 2007

(65) Prior Publication Data

US 2009/0064380 P1 Mar. 5, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—June Hwu
(74) *Attorney, Agent, or Firm*—Baker Manock & Jensen, PC

(57) ABSTRACT

A new and distinct variety characterized by red-colored nearly seedless grapes that ripens in late June, approximately two to three weeks earlier than the Flame Seedless Grape (unpatented) when grown in the San Joaquin Valley of Central California. The grapes of this new variety are produced on strong woody stems and branches that are well adapted to commercial handling.

1 Drawing Sheet

Latin name of the genus and species of the plant claimed: The claimed plant relates to a new and distinct variety of *Vitis vinifera* to be known as 'Sheegene-8'.

Variety denomination: This invention relates to a new discovery and asexual reproduction of a new variety of *Vitis vinifera*. The new variety was first hybridized by Timothy P. Sheehan of Porterville, Calif. in Spring 2000; first flowering occurred in May 2003. The pollen parent is Brickeys Best (unpatented) and the seed parent is Red Globe (U.S. Plant Pat. No. 4,787). The new variety was asexually propagated in the dormant season of 2003/2004, bud grafted on Harmony, virus free rootstock, in a *Vitis vinifera* variety block located near Fowler, Calif. on the west side of Thompson Road, north of Adams Road. The red-colored nearly seedless grapes produced by the new variety are medium in size, possibly smaller than Flame Seedless (unpatented), and mature at least two to three weeks before Flame Seedless (unpatented). The new variety has been shown to maintain its distinguishing characteristics through asexual propagation.

The new variety is distinguished from its pollen parent, Brickeys Best (unpatented), in that the new variety produces oval-shaped seedless grapes, as compared to the round-shaped seedless grapes produces by the pollen parent Brickeys Best. The new variety is distinguished from its seed parent, Red Globe (U.S. Plant Pat. No. 4,787), in that the new variety produces seedless grapes, as compared to its seed parent Red Globe (U.S. Plant Pat. No. 4,787), that produces seeded grapes.

BACKGROUND OF THE INVENTION

The present invention relates to a new and distinct variety of grape which will hereinafter be denominated as 'Sheegene-8' and more particularly as a grapevine which produces a red-colored nearly seedless grape that matures approximately during the fourth week of June in the San Joaquin Valley of Central California. The new invention most closely resembles Flame Seedless (unpatented) but it produces a slightly smaller medium size grape that is sweet, has very good flavor, and matures at least two to three weeks earlier.

SUMMARY OF THE INVENTION

The 'Sheegene-8' grapevine is characterized by producing a medium size red nearly seedless grape with very good flavor that is mature for harvesting and shipment approximately during the fourth week of June in the San Joaquin Valley of Central California. The new variety can be compared to Flame Seedless (unpatented) but the grapes mature at least two to three weeks earlier, among other distinguishing characteristics.

BRIEF DESCRIPTION OF THE DRAWINGS

The accompanying drawing is a colored photograph of the grapes produced by the subject variety; several leaves are displayed as well as a typical section of the vine. Across the top of the color photograph to the left is a mature leaf displaying the upper surface; in the lower center is a small branch with small leaves and bifurcate tendrils; and to the right is a mature leaf displaying the lower surface. Across the middle of the color photograph on the left is a mature grape cluster; and in the lower center are four grapes cut in half longitudinally as well as horizontally displaying the flesh and shape. Below the mature grape cluster on the left is a secondary growth cluster. Across the bottom of the color photograph to the left is secondary growth cluster; and in the center and to the right is a mature cane displaying nodes, and leaves.

DETAILED BOTANICAL DESCRIPTION

Referring more to the horticultural description of the new and distinct variety of grapevine, the following has been observed under the ecological conditions prevailing at the origin vineyard that is located east of the town of Fowler, Calif. in the San Joaquin Valley of Central California.

All major color descriptions are by reference to the Dictionary of Color by Maerz and Paul, First Edition, published in 1930. Common color names are also used in several instances.

VINE

Size: 5 feet (1.52 meters) in height, 38.19 inches (97 cm) in width.
Vigor: Very good.
Chilling requirements: Normal for grapevine in the San Joaquin Valley of Central California.
Figure: With wide cordons, forming a T-shape.
Productive capacity: Very good.
Regularity of bearing: Regular.

TRUNK

Size: 8.5 inches (22 cm) in circumference, 12 inches (30.48 cm) above graft.
Surface texture: Rough, shaggy.
Color bark: Pl.7 H9 — Liver Brown and Autumn Oak.
Mature canes color: Pl.12 K3 Cloudy Amber.
Nodes: 5 nodes on canes, 15¾ inches (40.01 cm).
Length between nodes: 3 to 4½ inches (7.62 to 11.43 cm).
Lenticel number: 0.
Lenticel size: 0.
Shoot size: Medium.
Shoot length: 3 to 3¼ inches (7.62 to 8.89 cm).
Shoot contour: Drooping.
Tendril number: 5.
Tendril length: 3 to 4 inches (7.62 to 10.16 cm).
Tendril location: At nodes.
Tendril form: Bifurcate.
Tendril texture: Soft to firm.
Bud shape: Triangular (convex).
Bud size: Small; ⅛ inch (3 mm) by ⅛ inch (3 mm).
Bud fruitfulness: Very good.
Bud break date: N/A.

BRANCHES

Size: 3 inches in circumference (7.62 cm).
Cordons: 38.19 inches (97 cm) from trunk.
Surface texture: Slightly tough.
Color (one year or older wood): Pl.6 L6 Chianti Antique Ruby.
Color (immature branches): Pl.20 K6 Piquant Green.
Surface texture: Immature growth smooth.
Lenticel number: 0.
Lenticel size: 0.

LEAVES

Size: Medium.
Density: Dense.
Average length: 4½ to 5 inches (11.43 to 12.7 cm).
Average width: 4½ to 5 inches (11.43 to 12.7 cm).
Form: Pentagonal.
Texture: Upper surface is smooth; lower surface is glabrous.
Color (upwardly disposed surface): Pl.23 J8 Mt. Vernon gr.
Color (leaf vein): Pl.20 K6 Piquant gr.
Marginal form: Slightly undulate.
Leaf vein thickness: 0.079 inches (2 mm).
Leaf margin: Tooth.
Glandular characteristics: None.
Petiole size: Large.
Petiole length: 2¾ to 6 inches (6.99 to 15.24 cm).
Petiole thickness: 0.079 to 0.12 inches (2 to 3 mm).
Petiole color: Pl.20 K6 — Piquant gr.
Petiole sinus form: Upside down 'U' shape.
Stem gland form: 0.
Stem gland position: 0.
Stem gland pattern: 0.
Lobes: Average is 4.
Teeth size: 0.625 inches (15 mm) by 0.625 inches (15 mm).
Teeth number: 3 between lobes.
Teeth shape: Convex.

INFLORESCENCE

Size: Cluster is 8½ to 9 inches (20.96 to 22.86 cm) in length.
Number borne per spur: Two.
Number borne per vine: 20 to 25.

FLOWERS

Flower buds (size): Small.
Flower buds (surface): Glabrous.
Flower buds (quantity): Moderate.
Date of bloom: Apr. 24, 2007.
Date of full bloom: May 3, 2007.
Size of bloom: 0.12 inches (3 mm).
Petal color: Pl. 19 K10.
Petal size: Small; 0.04 to 0.08 inches (1 to 2 mm).
Pistil color: Pl. 17 L7 — Viridine y.
Amount of pollen: No Data Available.
Date of first visible berries: May 3, 2007.

FRUIT

Solids: 20.3° Brix.
Acids: 0.44.
Sugar/acid ratio: 46.1.
Juice pH: 3.73.
Seeds: Rudimentary and very small.
Seed number: 2.
Capstem pedicel: 0.31 to 0.39 Inches (8–10 mm).
Berry weight: Approximately 4.05 grams.
Juice color: Pl.4 I-9 Marsh Rose.
Cluster size: Generally medium to large.
Cluster length: Average length not including main stem of cluster is 8.27 inches (21 cm).
Cluster width: Average diameter at greatest width is 5.97 inches (15 cm).
Cluster weight: 692 grams (25.1 oz. or 1 lb. 9 oz.).
Cluster form: Conical.
Stem: Generally 3 inches (7.62 cm).
Stem caliper: 0.5 inches (1.27 cm).
Berry size: Medium.
Berry size (average dimension along longitudinal axis): 0.86 inches (22 mm).
Berry size (average dimension along transverse axis): 0.79 inches (20 mm).
Berry form: Ovate.
Berry numbers: 175.

SKIN

Thickness: Thin.
Texture: Tough.
Tendency to crack: Unknown.
Blush color: Pl.56 I10 Catawba.
Ground color: Pl.55 J12 Dahlia Dr.
Pulp: Clear to Pl.7 H10 Piccadilly Mauvewood J.
Lenticels: None.

FLESH

Color: Pl6 I8 Slate V.
Juice production: Very good.
Flavor: Very good.
Aroma: Mild.
Texture: Firm.
Ripening: Even.
Eating quality: Very good.
Use: Fresh market.
Keeping quality: Good.
Resistance to disease: None observed.
Harvesting: Late June in the San Joaquin Valley of Central California.
Shipping and handling qualities: Very good.
U.S.D.A hardiness zone: Zones 8 and 9.

Having thus described and illustrated our new variety of grapevine, I claim:

1. A new variety of grapevine to be known as 'Sheegene-8', substantially as illustrated and described, characterized principally by its production of red-colored nearly seedless grapes, that mature approximately two to three weeks earlier in the season of ripening than does the Flame Seedless Grape (unpatented) that it closely resembles.

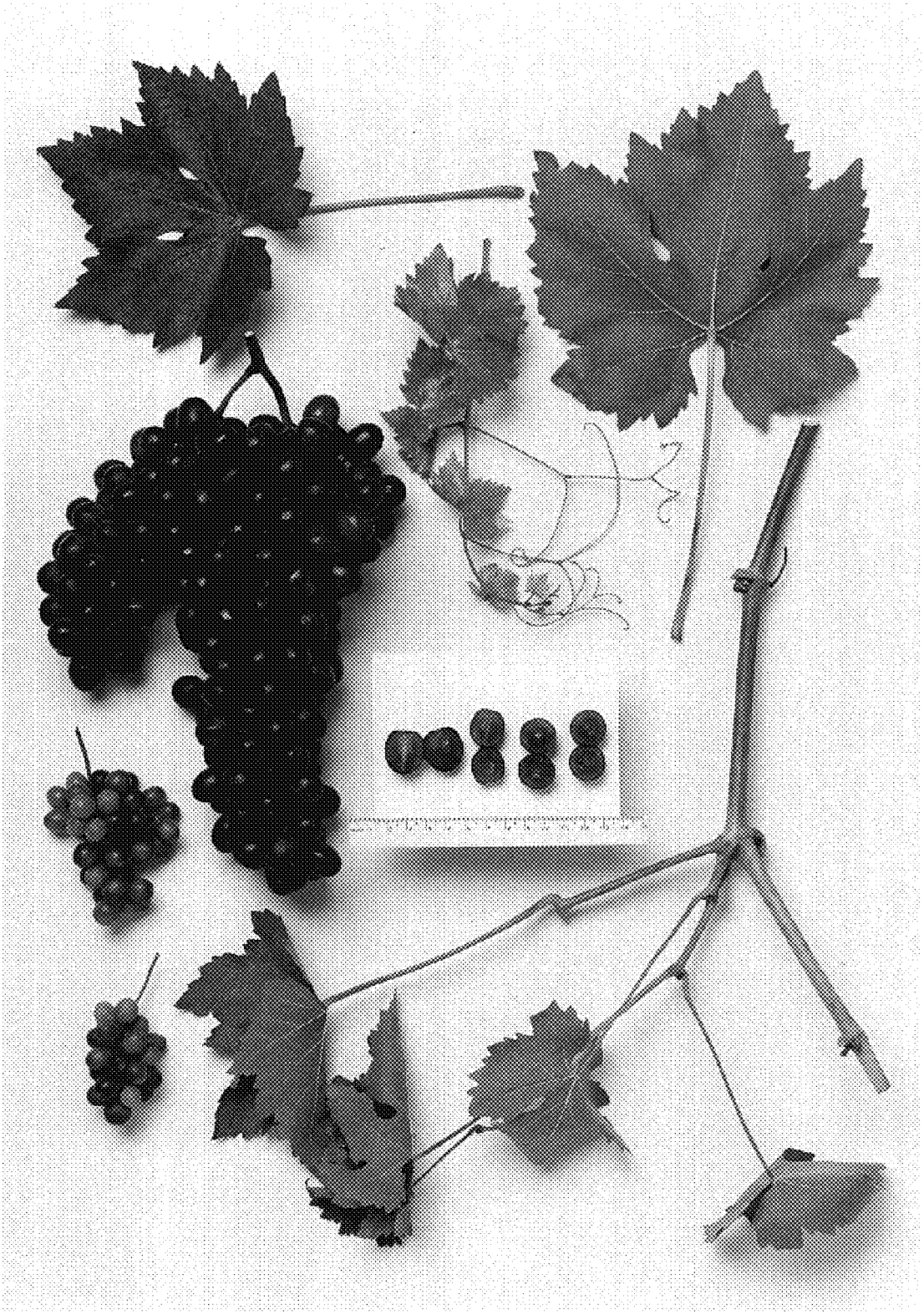

* * * * *